US008725526B2

(12) United States Patent
Cobbs et al.

(10) Patent No.: US 8,725,526 B2
(45) Date of Patent: May 13, 2014

(54) METHODS, SYSTEMS, AND APPARATUS FOR PROVIDING REAL TIME QUERY SUPPORT AND GRAPHICAL VIEWS OF PATIENT CARE INFORMATION

(75) Inventors: Archie Cobbs, Birmingham, AL (US); Gary York, Hoover, AL (US)

(73) Assignee: McKesson Information Solutions LLC, San Francisco, CA (US)

( * ) Notice: Subject to any disclaimer, the term of this patent is extended or adjusted under 35 U.S.C. 154(b) by 1707 days.

(21) Appl. No.: 11/255,145

(22) Filed: Oct. 20, 2005

(65) Prior Publication Data
US 2007/0094046 A1    Apr. 26, 2007

(51) Int. Cl.
*G06Q 50/00* (2012.01)
*G06Q 10/00* (2012.01)

(52) U.S. Cl.
USPC .................................................. 705/2; 705/3

(58) Field of Classification Search
USPC .......................................................... 705/2–3
See application file for complete search history.

(56) References Cited

U.S. PATENT DOCUMENTS

| | | |
|---|---|---|
| 4,135,241 A | 1/1979 | Stanis et al. |
| 4,807,155 A | 2/1989 | Cree et al. |
| 4,994,908 A | 2/1991 | Kuban et al. |
| 5,319,363 A | 6/1994 | Welch et al. |
| 5,331,549 A | 7/1994 | Crawford et al. |
| 5,452,808 A | 9/1995 | Abramowitz |
| 5,716,350 A | 2/1998 | Ryan |
| 5,748,907 A | 5/1998 | Crane |
| 5,760,704 A | 6/1998 | Barton et al. |
| 5,781,442 A | 7/1998 | Engleson et al. |
| 5,802,494 A | 9/1998 | Kuno |
| 5,946,659 A | 8/1999 | Lancelot et al. |
| 6,078,261 A | 6/2000 | Davsko |
| 6,314,556 B1 | 11/2001 | DeBusk et al. |

(Continued)

FOREIGN PATENT DOCUMENTS

| | | |
|---|---|---|
| EP | 1 310 895 A2 | 5/2003 |
| WO | WO 91/06917 A | 5/1991 |

(Continued)

OTHER PUBLICATIONS

Enterprise Patient Care Visibility Solutions, Patient Care Communication Board, Awarix, Inc., http://www.awarix.com/products.html.

(Continued)

*Primary Examiner* — Minnah Seoh
(74) *Attorney, Agent, or Firm* — Sutherland Asbill & Brennan LLP

(57) ABSTRACT

The present disclosure relates to methods, systems, and apparatus for providing query support for a real-time patient care graphical view. Location information associated with one or more patients and information associated with at least one indicator of care of at least one of the patients may be received. A graphical user interface may display the location information associated with the patients and the at least one indicator of care of at least one of the patients in a geospatial arrangement. The graphical user interface may be updated when a change occurs in either the location information associated with the patients or the at least one indicator of care of at lease one of the patients. In addition, a user query for the location information associated with each of the patients receiving care from a physician may be received and output in the geospatial arrangement via the graphical interface.

20 Claims, 6 Drawing Sheets

(56) References Cited

U.S. PATENT DOCUMENTS

| | | | |
|---|---|---|---|
| 6,356,874 B1 | 3/2002 | Øhrn et al. | |
| 6,662,050 B2 | 12/2003 | Olson | |
| 6,701,345 B1 | 3/2004 | Carley et al. | |
| 7,716,066 B2 | 5/2010 | Rosow et al. | |
| 7,720,695 B2 | 5/2010 | Rosow et al. | |
| 7,734,479 B2 | 6/2010 | Rosow et al. | |
| 7,756,723 B2 | 7/2010 | Rosow et al. | |
| 7,774,215 B2 | 8/2010 | Rosow et al. | |
| 7,890,347 B2 | 2/2011 | Rosow et al. | |
| 7,953,610 B2 | 5/2011 | Rosow et al. | |
| 2001/0042135 A1 | 11/2001 | Lewis | |
| 2002/0013714 A1 | 1/2002 | Dubler et al. | |
| 2002/0042745 A1 | 4/2002 | Nacey | |
| 2002/0044043 A1 | 4/2002 | Chaco et al. | |
| 2002/0091309 A1 | 7/2002 | Auer | |
| 2002/0116226 A1 | 8/2002 | Auer et al. | |
| 2002/0158919 A1 | 10/2002 | Nacey | |
| 2002/0183979 A1* | 12/2002 | Wildman | 702/188 |
| 2003/0074222 A1* | 4/2003 | Rosow et al. | 705/2 |
| 2003/0078810 A1 | 4/2003 | Cole et al. | |
| 2004/0046020 A1* | 3/2004 | Andreasson et al. | 235/385 |
| 2004/0078231 A1* | 4/2004 | Wilkes et al. | 705/2 |
| 2004/0167804 A1 | 8/2004 | Simpson et al. | |
| 2004/0243446 A1 | 12/2004 | Wyatt | |
| 2005/0219059 A1 | 10/2005 | Ulrich et al. | |
| 2005/0242946 A1 | 11/2005 | Hubbard et al. | |
| 2005/0283382 A1 | 12/2005 | Donoghue et al. | |
| 2006/0004605 A1* | 1/2006 | Donoghue et al. | 705/2 |
| 2006/0049936 A1 | 3/2006 | Collins, Jr. et al. | |
| 2006/0114888 A1 | 6/2006 | Schuman | |
| 2006/0143045 A1 | 6/2006 | Nacey | |
| 2006/0167738 A1 | 7/2006 | Spear et al. | |
| 2006/0247948 A1* | 11/2006 | Ellis et al. | 705/2 |
| 2007/0094045 A1 | 4/2007 | Cobbs et al. | |
| 2008/0164998 A1 | 7/2008 | Scherpbier et al. | |
| 2009/0315735 A1 | 12/2009 | Bhavani et al. | |
| 2013/0311516 A1 | 11/2013 | Callans et al. | |

FOREIGN PATENT DOCUMENTS

| | | |
|---|---|---|
| WO | WO 97/25682 A | 7/1997 |
| WO | WO 98/50871 A | 11/1998 |
| WO | 2007047052 A2 | 4/2007 |

OTHER PUBLICATIONS

International Search Report and Written Opinion for PCT/US2006/037573, issued Jan. 17, 2007.
International Search Report and Written Opinion for PCT/US2006/037755, issued Aug. 27, 2007.
"Subnotebooks, Phones and More. St. Vincent's Gets on Track," Mobile Health Data [Online], pp. 1-2, Nov. 19, 2004, obtained from http://www.awarix.com on Jul. 2, 2007.
"Coping with Information Overload," The News Source for Healthcare Information Technology [Online], pp. 1-2, Nov. 2004, obtained from http://www.awarix.com on Jul. 2, 2007.
St. Vincent's first to use Birmingham startup's information system, The Birmingham News [Online], pp. 1-3, Apr. 11, 2005, obtained from http://www.awarix.com on Jul. 2, 2007.
D Lockridge, "St. Vincent's is Digital Flagship," Birmingham Medical News [Online], pp. 1-3, Sep. 2005, obtained from http://www.awarix.com on Jul. 2, 2007.
"Two Automatic Identification Technology, neither new in the sense of being recent developments . . . ," Patient Safety & Quality Healthcare [online], pp. 1-4, Aug. 2005, obtained from http://www.awarix.com on Jul. 2, 2007.
G.M. Jacquez et al., "Design and Implementation of Space-Time Intelligence System for Disease Surveillance," Journal of Geographical Systems: Geographical Information, Analysis, Theory and Decision, Springer-Verlag, BE, vol. 7, No. 1, pp. 7-23, May 1, 2005.
Disclosure Statement Under 37 C.F.R. § 1.56 for U.S. Appl. No. 11/255,145.
Final Office Action for U.S. Appl. No. 11/255,115 mailed Sep. 16, 2009.
Non-Final Office Action for U.S. Appl. No. 11/255,115 mailed May 27, 2009.
Non-Final Office Action for U.S. Appl. No. 11/255,115 mailed Jan. 10, 2012.
Final Office Action for U.S. Appl. No. 11/255,115 mailed May 31, 2012.
International Search Report and Written Opinion for PCT/US2012/025158, issued Jun. 12, 2013.
Non-Final Office Action for U.S. Appl. No. 11/255,115 mailed Jun. 19, 2013.
Notice of Allowance for U.S. Appl. No. 11/255,115 mailed Dec. 4, 2013.

* cited by examiner

METHODS, SYSTEMS, AND APPARATUS FOR PROVIDING REAL TIME QUERY SUPPORT AND GRAPHICAL VIEWS OF PATIENT CARE INFORMATION

FIELD OF THE INVENTION

The invention relates generally to the field of health care, and more particularly, relates to methods, systems, and apparatus for providing real time query support and graphical views of patient care information.

BACKGROUND OF THE INVENTION

Health care settings such as hospitals can involve relatively complex information and work flows. Health care workers can serve in a wide variety of roles and work in many different physical locations across a hospital or other enterprise. Some workers, such as physicians, can be very mobile. As would be expected in such an environment, effective communication among workers can be essential for the overall operation of a hospital or other enterprise to be coherent and productive.

Different users can have different information needs, and often times those needs may require relatively specialized, custom views of information about patient care, patient flow, or resource utilization. These unique needs may be satisfied through a query of an information database or other data storage device which can contain information about the patient care process. The query can provide a set of results as items, such as a set of patients, rooms, or beds. Many conventional systems may support such specialized queries of databases and other data storage devices, and may display the query results in a tabular form. In some instances, a particular query may be repeated by a user to periodically update the display to show any changes in the query results.

These types of queries and user interfaces can have drawbacks. For example, query results from these conventional systems can be time consuming to read and use. In some instances, relatively important information or other particularly relevant information in a query result may not be readily apparent or may appear later in the query results.

Therefore, a need exists for methods, systems, and apparatus for providing real time query support and graphical views of patient care information.

A further need exists for methods, systems, and apparatus for providing a graphical user interface for real time query support for patient care.

Yet a further need exists for providing methods, systems, and apparatus for providing real time information for patient care in a health care environment.

SUMMARY OF THE INVENTION

Some or all of the needs can be addressed by embodiments of the present invention. Embodiments of the present invention can improve communications and information flow in a health care environment, such as a hospital or assisted care facility, using one or more graphical user interfaces located within the health care environment, such as on walls, in patient rooms, and adjacent to areas where health care personnel may work or otherwise be stationed. Such interfaces can display various pieces of graphical-type information in a geospatial arrangement such as a map, including a patient's location, an indicator of care of the patient, a status of rooms in a particular area or department. The information provided by such graphical user interfaces can be readily available to a user or health care personnel and can be updated in real time as a change to the information is made, detected, or otherwise received by the present invention.

In some instances, users may be interested in obtaining specific information, and can submit a user query for selected information via a computer system. Other types of queries can be based at least in part on contextual-type information associated with a user or a patient, such as a user's role, or a location of a particular client device. Frequently used queries can be stored, formatted, and retrieved by a user for subsequent use. Information received in response to a user query can be graphically displayed via a graphical user interface in a graphical representation. The graphical representation permits information to be displayed with relatively greater information density, and permits users to rapidly view and comprehend such information. Various graphical views of the information can be displayed and updated in real time to show changes in events and activities associated with care of the patients.

One aspect of the invention can include a method for providing information associated with care of a patient in a health care environment. The method includes receiving location information associated with a patient, and receiving information associated with at least one indicator of care of the patient. The method also includes providing a graphical user interface capable of displaying the location information associated with the patient and the at least one indicator of care of the patient in a geospatial arrangement. In addition, the method includes displaying in a geospatial arrangement via the graphical user interface the location information associated with the patient, and the at least one indicator of care of the patient. Furthermore, the method includes updating the graphical user interface when a change occurs in either the location information associated with the patient or the at least one indicator of care of the patient.

Another aspect of the invention can include a method for providing a result to a user query for information associated with care of a patient in a health care environment. The method includes receiving information associated with a patient in a health care environment, such as a location associated with the patient and an indicator of care of the patient. In addition, the method includes providing a graphical user interface capable of displaying the location associated with a patient and the indicator of care of the patient in a geospatial arrangement. Moreover, the method includes receiving a query from a user for information associated with the patient. Furthermore, the method includes in response to the query, displaying via the graphical user interface a geospatial arrangement of the location associated with a patient and the indicator of care of the patient. The method also includes when a change occurs in either the location associated with a patient or the indicator of care of the patient, updating the location associated with a patient or the indicator of care of the patient displayed by the graphical user interface.

Yet another aspect of the invention can include a system for tracking a patient and monitoring care of the patient in a health care environment. The system includes an output device capable of displaying a location associated with the patient and an indicator of care of the patient in a geospatial arrangement. The system also includes a query support engine capable of receiving information associated with the patient in a health care environment, such as a location associated with the patient and an indicator of care of the patient. Moreover, the query support engine is further capable of receiving a query for a portion of the information associated with the patient. In addition, the query support engine is capable of, in response to the query, displaying in a geospatial arrangement via the output device, the location associated with the patient and an indicator of care of the patient. Furthermore, the query support engine is capable of, when a change in the location associated with the patient or the indicator of care of the patient occurs, updating the geospatial arrangement.

Another aspect of the invention can include a user interface for tracking a patient and monitoring care of the patient in real time in a health care environment. The user interface can include a geospatial view of a health care environment. In addition, the user interface can include a plurality of indicators associated with respective locations associated with a plurality of patients in the health care environment. Furthermore, the user interface can include a plurality of indicators associated with care of the plurality of patients in the health care environment.

Other embodiments of the invention can provide information associated with care of a patient in a health care environment. Yet other embodiments of the invention can provide a result to a user query for information associated with care of a patient in a health care environment. In addition, other embodiments of the invention can track a patient and monitoring care of the patient in a health care environment. In addition, other embodiments of the invention can provide a user interface for tracking a patient and monitoring care of the patient in real time in a health care environment.

Other aspects and embodiments of systems, methods, and apparatuses according to the invention are apparent from the following detailed description of the disclosed embodiments and the appended drawings and claims.

DETAILED DESCRIPTION OF EMBODIMENTS

Figure 1:
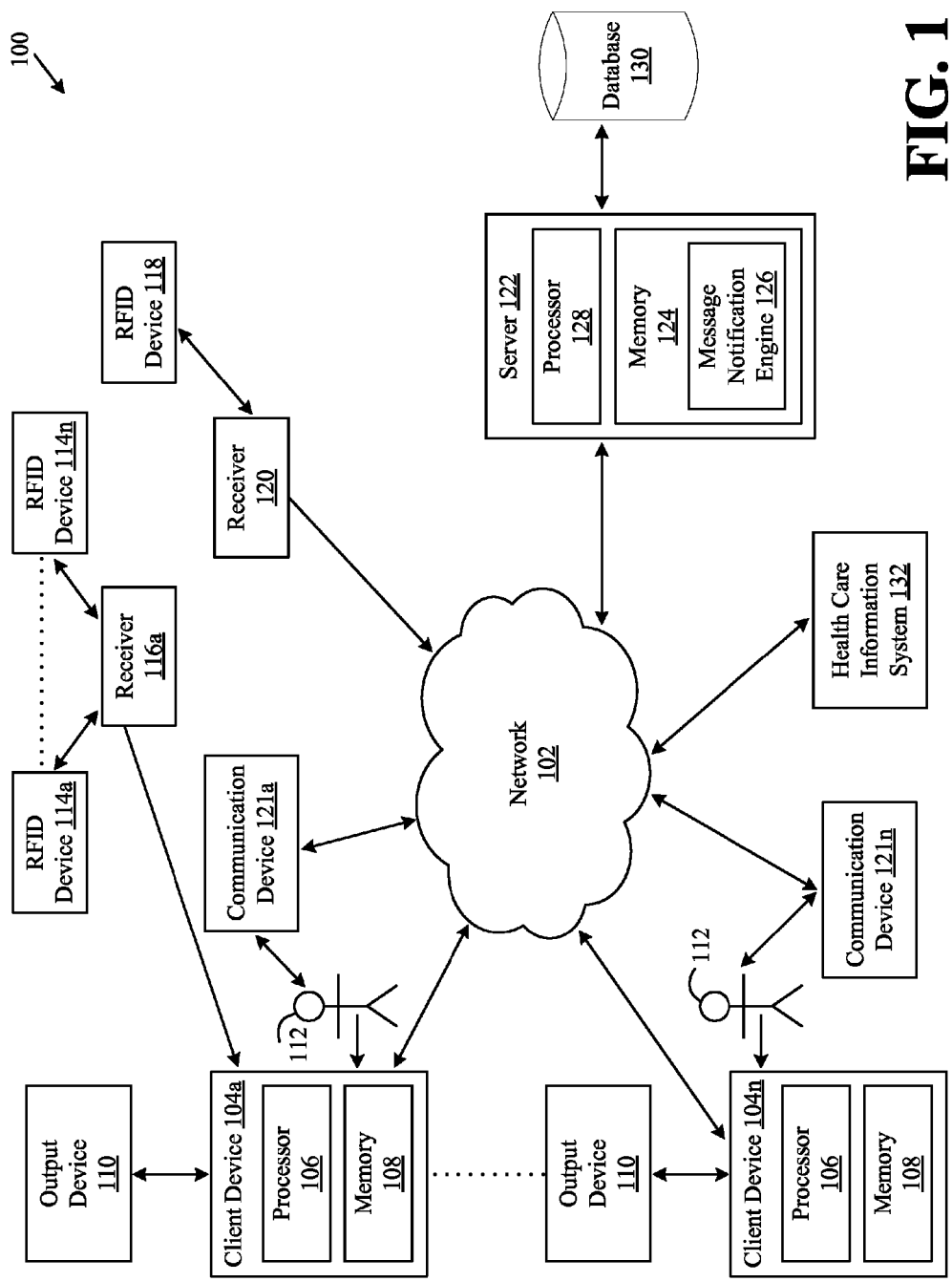
FIG. 1 is an exemplary system in accordance with an embodiment of the invention.

Various embodiments of the invention address some or all of the above issues and combinations thereof. They do so by providing methods, systems, and apparatuses for providing real time query support and graphical views of patient care information. At least one embodiment can provide a graphical user interface that provides location information and health care status information for a patient in a health care environment. User queries for a particular patient can be displayed on the graphical user interface, and the graphical user interface can be updated in real time when a change to the patient's location or health care status is made. By providing real time and updated location information and health care status information for a patient in a health care environment, health care personnel can monitor the patient and any changes to the location or health care status of the patient. Furthermore, providing graphical responses to a user's query for patient-related information can facilitate more immediate and improved responses to the patient's health care needs as well as facilitate improved management and prioritization of health care resources and personnel.

An "item", as used within this specification, is defined as any area, object, or person in a health care environment, such as a hospital. Examples of an item can include, but are not limited to, a room, an area, a patient, a bed, a gurney, a wheelchair, a walker, a health care worker, or any category or group of items by which such items can be organized.

An "event", as used within this specification, is defined as an activity during any instance or duration of time. Examples of an event can include, but are not limited to, a patient care activity or event, an activity that occurs in a health care environment; an activity capable of being tracked by a health care information system, such as an admission, transfer or discharge of a patient, or the creation of an order or result associated with a patient; completion of an activity or series of activities, an indication by a user via a client device that particular information should be removed, modified or updated; expiration of an item over a period of time; expiration of a preset time; the presence or absence of a patient or staff member in a certain physical area; a patient's falling; a change in the patient location; and an event notification from a patient monitoring device, such as a heart rate monitor.

"Location information", as used within this specification can include, but is not limited to, a coordinate, a set of coordinates, a set of geographic coordinates, a set of Cartesian coordinates, a geo-location, a room or area, a floor, a building, a distance from an object, a distance from a person, a position, a location, a position in a room or area, and a position on a floor or building.

An "indicator of care of a patient", as used within this specification can include, but is not limited to, an order, a request, an approval, an approval of a prescription, a lab result, a safety indicator, a limit, a range, a warning, a statistic, a health status, a date, a time, a timer, contact information, a health-related statistic, a body function, patient care information, a patient care state, a special patient care state, and a patient care activity.

The term "geospatial arrangement", as used within this specification is defined as the organization of data or information relative to a map or map-type view of a particular area.

Figure 2:
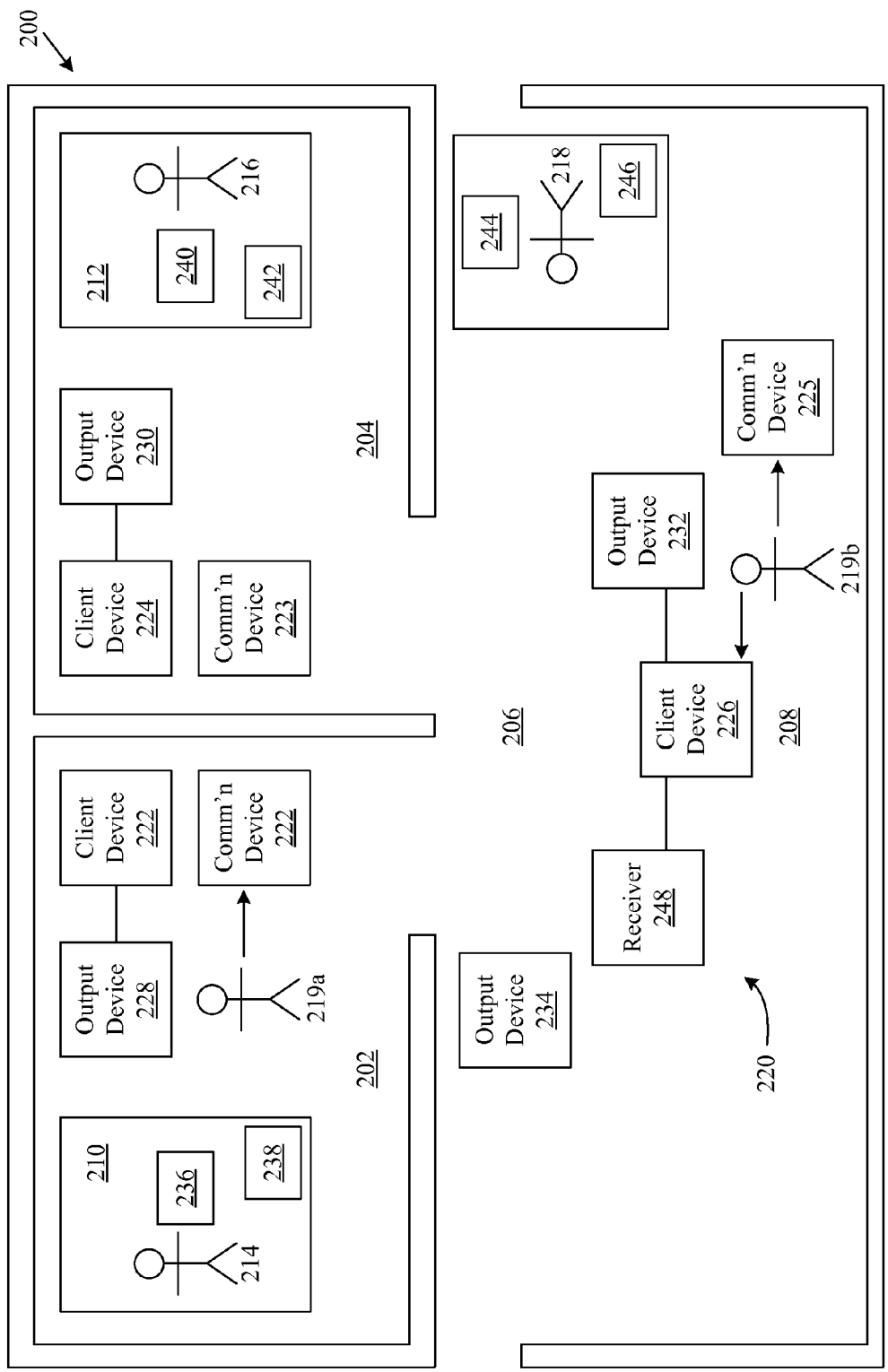
FIG. 2 is an example of an environment in which the system of FIG. 1 can operate in accordance with an embodiment of the invention

FIG. 1 is an exemplary system in accordance with various embodiments of the invention. The system shown is by way of example, and the system can operate in a variety of environments, such as a health care environment or a hospital. One example of a health care environment is shown in FIG. 2. Referring back to FIG. 1, a system 100 is shown with a communications network 102 in communication with at least one client device 104*a*. Any number of other client devices 104*n* can also be in communication with the network 102. The communications network 102 shown in FIG. 1 can be a wireless communications network. Other types of communications networks can be used in accordance with various embodiments of the invention.

Each client device 104*a-n* can be a computer or processor-based device capable of communicating with the communications network 102 via a signal, such as a wireless frequency signal or a direct wired communication signal. Each client device, such as 104*a*, can include a processor 106 and a computer-readable medium, such as a random access memory (RAM) 108, coupled to the processor 106. The processor 106 can execute computer-executable program instructions stored in memory 108. Such processors may comprise a microprocessor, an ASIC, and state machines. Such processors comprise, or may be in communication with media for example, computer-readable media, which stores instructions that, when executed by the processor, cause the processor to perform the steps described herein. Embodiments of computer-readable media include, but are not limited to, an electronic, optical, magnetic, or other storage or transmission device capable of providing a processor, such as the processor 106, with computer-readable instructions. Other examples of suitable media include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. The instructions may comprise code from any computer-programming language, including, for example, C, C++, C#, Visual Basic, Java, Python, Perl, and JavaScript.

Client devices 104a-n may also comprise a number of external or internal devices such as a mouse, a CD-ROM, DVD, a keyboard, a display, or other input or output devices. As shown in FIG. 1, a client device such as 104a can be in communication with an output device, such as 110. Examples of client devices 104a-n are personal computers, mobile computers, handheld portable computers, digital assistants, personal digital assistants, cellular phones, mobile phones, smart phones, pagers, digital tablets, desktop computers, laptop computers, Internet appliances, and other processor-based devices. In general, a client device, such as 104a, may be any type of processor-based platform that is connected to a network, such as 102, and that interacts with one or more application programs. Client devices 104a-n may operate on any operating system capable of supporting a browser or browser-enabled application, such as Microsoft® Windows® or Linux. The client devices 104a-n shown include, for example, personal computers executing a browser application program such as Microsoft Corporation's Internet Explorer™, Netscape Communication Corporation's Netscape Navigator™, and Apple Computer, Inc.'s Safari™.

A user, such as 112, can interact with a client device, such as 104a, via an input device (not shown) such as a keyboard or a mouse. For example, a user can input information, such as location information associated with a patient, information associated with an indicator of care of a patient, or other information associated with a particular patient, via the client device 104a by keying text via a keyboard or inputting a command via a mouse, or using a stylus or using a bare finger. In another example, a user can input a user query for a patient care information via the client device 104a by keying text via a keyboard or inputting a command via a mouse. In one embodiment, a user 112 can input one or more commands via a client device 104a to select one or more desired items or other information for display via an output device, such as 110. A user 112a can also input one or more commands via a client device 104a to configure a graphical user interface for an output device, such as selecting a desired geospatial arrangement of items or other information for the graphical user interface.

A user such as 112 can receive output, such as a query response with patient care information or other information associated with a particular patient information, from an output device, such as 110, via a client device. In one embodiment, information such as location information associated with a patient and a status of care for a patient can be displayed on an output device 110. One suitable output device is a display device capable of displaying information in a geospatial arrangement on a graphical user interface. Another suitable output device is an Awarix™ patient care communication display board capable of displaying location information associated with a patient, an indicator of care of a patient, or other patient process care information on a map, geospatial-type view, table, or grid-type view. Other types of output devices can include, but are not limited to, private-type displays, public-type displays, plasma displays, LCD displays, touch screen devices, and projector displays on cinema-type screens. In some embodiments, the Scalable Vector Graphics ("SVG") standard for describing graphical information, or a similar suitable standard or technique, may be utilized as part of the graphical rendering process. An example of a suitable graphical user interface for an output device is shown and described below in FIG. 3.

In one embodiment, multiple output devices such as public-type displays or flat screen monitors can be mounted in a health care environment, such as in rooms, hallways, on doors, in central monitoring areas, or other areas where users or health care personnel may work, be stationed, or otherwise desire information associated with a patient's location or patient's health care status. In other embodiments, an output device such as private-type display or a computer display monitor can be connected to or associated with a client device, such as a handheld portable computer device or a desktop personal computer (PC).

In the embodiment shown in FIG. 1, a device, such as RFID device 114a, capable of providing location information associated with a patient can be in communication with a client device, such as 104a. A corresponding receiver, such as 116a, capable of receiving location information associated with a patient can interface or otherwise facilitate communication between the RFID device 114a and the client device 104a. Multiple devices, such as 114a-n, capable of providing location information associated with respective patients can also be in communication with a client device, such as 104a, via the same receiver, such as 116a, or any number of other receivers. Other receivers, such as 116n, capable of receiving location information associated with a patient can interface or otherwise facilitate communication between any number of devices capable of providing location information associated with respective patients and a client device. A suitable device capable of providing location information associated with a patient can be a radio frequency identification device (RFID), and a suitable receiver capable of receiving location information associated with a patient can be a RFID reader. Other types of devices and technologies capable of providing location information associated with a patient can be used with other embodiments of the invention, including, but not limited to, passive-type RFID, active-type RFID, wireless, infrared, global positioning satellite (GPS)-type devices or other devices capable of providing location information associated with a patient or otherwise facilitating determination of a location associated with a patient, staff member, or piece of medical equipment.

In at least one embodiment, a device capable of providing location information associated with a patient, and a corresponding receiver capable of receiving location information associated with a patient can communicate with a client via a network. For example as shown in FIG. 1, RFID device 118 and receiver 120 can communicate with client device 104a via the network 102. In another embodiment, a device capable of providing location information associated with a patient can communicate with both the network 102 and one or more client devices 104a-n, either with or without a corresponding receiver capable of receiving location information associated with a patient. In some instances, a receiver capable of receiving location information associated with a patient can be incorporated into or otherwise associated with a client or another device associated with a network. In any of these instances, a device capable of providing location information associated with a patient and a corresponding receiver capable of receiving location information associated with a patient can communicate the location information to a remote location via a network, such as 102.

In one embodiment, any type of wireless location tracking technology, such as active RFID, can be used to provide real time location information about one or more patients' locations in a health care environment. Such locations can be tracked automatically by a query support engine, such as 126 in FIG. 1 and described below, via the wireless location tracking technology as each patient moves throughout a health care environment, such as a hospital, floor, or room.

In one embodiment, each client device, such as 104a-n, can be associated with a unique identifier. Examples of suitable identifiers are serial numbers, Ethernet MAC addresses, IP addresses, numbers generated via random and/or pseudo-random algorithms etc. A database, such as 130 in FIG. 1 and described below, or other data storage devices can store the unique identifiers for subsequent retrieval. In this manner, the system 100 can record the location of a client device, such as 104a or a desktop computer, so that the display configuration for an associated output device, such as 110, can be changed based on the location of the client device or desktop computer. For example, a client device or desktop computer on a third floor of a building in a health care environment may only be able to display information about patients on that particular floor. By associating a unique identifier with each client device or desktop computer, the system 100 can track the location of each client device or desktop computer, and in particular mobile client devices, to support dynamic information display on the associated output device based on the current location of the particular client device.

The system 100 can also include a server 122 in communication with the network 102. The server 122 shown can include memory 124 and a query support application program, also known as a query support engine 126. In one embodiment, a query support engine 126 can receive location information associated with a patient from a device capable of providing location information associated with a patient, such as a RFID. The query support engine 126 can correlate the location information with any other information, such as an indicator of care of a particular patient, and cause the display of information on one or more output devices, such as 110.

Information associated with various indicators of care of multiple patients can be received by the server 122 via the network 102 from one or more client devices 104a-n, the database 130 or other data storage devices, from other information systems, and from health care information systems, such as an admission, discharge, and transfer (ADT)-type system. In one embodiment, information associated with an indicator of care of a patient can be input by a user 112, such as an attending physician, via a client device 104a, such as a handheld portable computer or desktop computer. The information can be received by the server 122 via the network 102 for processing by the query support engine 126 or storage by the database 130 or other data storage device. In another embodiment, information associated with an indicator of care of a patient can be received or otherwise obtained from a health care information system 132, database 130, or other data storage device or information source. The query support engine 126 can receive or obtain such information from such sources via the server 122 and the network 102.

The query support engine 126 can also permit a user, such as 112, to transmit a query for patient care information. For example, the query support engine 126 can provide functionality via a client device, such as 104a, to allow a user 112 to transmit a query to obtain information associated with a particular patient. The query support engine 126 can receive and process the query to generate a query response, for instance, a location associated with the patient and an indicator of care of the patient. The query support engine 126 is further capable of facilitating a geospatial arrangement and graphical display of information associated with a particular patient on an output device such as 110, for example, location information associated with the patient and an indicator of care of the patient. In one embodiment, the query support engine 126 can facilitate a display of graphical information on a graphical user interface in a geospatial arrangement on an output device, such as 110. The query support engine 126 can also facilitate the generation of graphical representations of information on a graphical user interface for an output device including text, icons, graphical elements, colors, timers, animation, or any combination thereof. When new or changed information is received by the query support engine 126, such as from a device capable of providing location information associated with a patient or a user input of an indicator of care of a patient, the query support engine 126 is capable of updating the information on a graphical user interface for the output device in real time by displaying some or all of the new or changed information. In addition, the query support engine 126 is capable of displaying any number of items in a particular health care environment, and formatting the items in any type of view provided on a graphical user interface for an output device, such as a map, geospatial-type view, table, or grid-type view. In this manner, a user can obtain and monitor selected patient care information in a geospatial arrangement on a graphical user interface for an output device, and view any new or changes to the information on the graphical user interface as they occur.

Similar to the client devices 104a-n, the server device 122 shown comprises a processor 128 coupled to a computer-readable memory 124. The server device 122 can be in communication with a database, such as 130, or other data storage device. The database 130 can receive and store data from the server 122, or from a client device, such as 104a, via the network 102. Data stored in the database 130 can be retrieved by the server 122 or client devices 104a-n as needed.

In one embodiment, a server 122 and the query support engine 126 can receive location information associated with a patient, information associated with an indicator of care of a patient, or other patient care information. The query support engine 126 can store some or all of the information in the database 130 or other data storage device for subsequent retrieval.

Server device 122, depicted as a single computer system, may be implemented as a network of computer processors. Examples of a server device 122 are servers, mainframe computers, networked computers, a processor-based device, and similar types of systems and devices. Client processor 106 and the server processor 128 can be any of a number of computer processors, such as processors from Intel Corporation of Santa Clara, Calif. and Motorola Corporation of Schaumburg, Ill. The computational tasks associated with rendering the graphical image could be performed on the server device(s) and/or some or all of the client device(s).

The server device 122 can integrate with and can communicate with other information systems in a health care environment to receive information, such as real time events associated with one or more patient care processes, and indicators of care of one or more patients. Such real time events and indicators can be stored in the query support database 130 or other data storage device to support real time and dynamic updating of information displayed on some or all of the output devices 110. As shown in FIG. 1, an information system such as a health care information system 132 can communicate with the server 122 via the network 102. In one embodiment, integration of the server 122 with other suitable information systems can be based on an industry standard HL7 communication model. In another embodiment, a custom integration of the server 122 with other suitable information systems can achieve similar results to an industry standard HL7 communication model. Examples of suitable information systems the server device 122 and other components of the system 100 can integrate with or otherwise communicate with can include, but are not limited to, an ADT-type (admission, discharge, and transfer) system, ordering systems, result reporting systems, lab-type systems, pharmacy-type systems, radiology-type systems, transcription-type systems, environmental services-type systems, and transportation-type systems.

FIG. 2 illustrates an example of an environment in which a system according to an embodiment of the invention can operate. By way of example, the system 100 in FIG. 1 can operate in the environment 200 shown. The environment 200 shown in FIG. 2 is a health care environment, such as a hospital or an assisted care facility. The environment 200 shown in FIG. 2 is by way of example, and illustrates a portion of a hospital or assisted care facility. The environment 200 shown includes multiple rooms 202, 204, 206, 208 or areas, and beds 210, 212 in some of the rooms 202, 204. Any number of patients, such as 214, 216, 218, can be within the environment 200 at any particular time. Two rooms 202, 204 shown adjacent to each other can be patient care rooms with a respective bed 210, 212 for each patient 214, 216 shown. A hallway or corridor 206 adjacent to rooms 202, 204 is also shown, with another patient 218 in the corridor 206. A monitoring area 208 can be adjacent to the corridor 206 and rooms 202, 204. A user 220 or health care worker is shown in the monitoring area 208. Embodiments of the invention can operate in any other configuration of rooms, corridors, central monitoring or orderly areas, or other rooms in a health care environment.

The system shown in FIG. 2 can operate similar to the system 100 shown and described in FIG. 1. The system 220 can include some or all of the system components shown in FIG. 1. In some instances, some or all of the components of the system 220 may be within the environment 200, and in other instances, some components of the system 220 may be outside of the environment 200. For example, system components not shown in FIG. 2 but which can be part of the system 220 can include a network, a server, and a query support engine, similar to like components described in FIG. 1.

The system 220 shown in FIG. 2 can also include client devices 222, 224, 226, associated output devices 228, 230, 232, 234, a series of devices 236, 238, 240, 242, 244, 246 capable of providing location information associated with a patient, and a device 248 capable of receiving location information associated with a patient. The components of system 220 described above can operate in a similar manner to the like components described in FIG. 1.

In the embodiment shown in FIG. 2, a patient can be associated with a device capable of providing location information associated with a patient by mounting a RFID tag or another type of location information type device to a chart associated with the patient. In some instances, a patient chart can accompany a patient as the patient moves within a health care environment, such as a hospital. A device capable of providing location information associated with a patient, such as a RFID tag, can be mounted to a patient chart associated with the particular patient. A device capable of providing location information associated with a patient can be mounted to other types of charts, documents, or other media associated with a particular patient in accordance with embodiments of the invention. In this manner, as a patient moves through a health care environment with an associated patient chart, the general location of the patient can be monitored by a query support engine, such as 126, via a receiver capable of receiving location information associated with the patient. The query support engine 126 can facilitate the graphical display of such information in a geospatial arrangement via a graphical user interface, such as 300, for an output device, such as 110. In one embodiment, a query support engine 126 can communicate with other information systems, such as an admissions, discharge, and transfer (ADT)-type system, to automatically receive new or modified patient bed assignment information when a new patient is admitted to or enters a health care environment, or when a patient is transferred from or discharged from a health care environment. The query support engine 126 can incorporate and display information received from other types of information systems with previously received location information associated with a patient and indicators of care of the patient.

In another embodiment, a patient can be associated with a device capable of providing location information associated with a patient by mounting a RFID tag or other location information type device to the patient. This can be accomplished by use of a wearable tag, band, chip, adhesive, implant, stamp, or other device or technique. A RFID or tag number can then be associated with the patient, and a query support engine, such as 126, can track the RFID, tag number, and patient associated with the RFID, tag, and tag number as the patient moves within a health care environment.

In yet another embodiment, a bed can be associated with a device capable of providing location information associated with a patient by mounting a RFID tag or other location information type device to the bed. When a patient is assigned a particular bed, the patient is associated with the bed, and therefore the associated with the device mounted to the bed. The association between a bed and a patient, also known as a patient bed assignment, can be tracked and managed using the system 100. In some instances, similar information can be received by a query support engine, such as 126, via an automated information system, such as an admission, discharge, transfer (ADT)-type system. In any instance, the system 100 via the query support engine 126 can incorporate and display information received from ADT-type systems and other similar systems, devices or techniques that track and manage patient bed assignment information. In this manner, a patient who is associated with a tag can be tracked using patient admission, transfer, and discharge information from ADT-type systems, and the system 100 can graphically display such information in a geospatial arrangement via a graphical user interface, such as 300, for an output device, such as 110.

As shown in FIG. 2, a client device 222, 224, 226 and associated output devices 228, 230, 232, 234, can be located in or adjacent to each room 202, 204, in a hallway or corridor, and in a remote or adjacent monitoring area 208. In other embodiments, an output device such as a display screen can be located on a door, wall, floor, ceiling, furniture, or other objects associated with a room or located in a room. In any instance, a user, such as 250, can receive information via an output device, such as 228, 230, 232, 234, including location information associated with a patient, an indicator of care of a patient, and other patient care information. A user 250 can also interact with a client device, such as 226, to input information associated with a patient, such as an indicator of care of a patient, or to submit a query or other request for information associated with a particular patient. Similar to the system 100 in FIG. 1, the system 200 in FIG. 2 can provide a query response to the user's query, such as displaying graphical information in a geospatial arrangement via a graphical user interface for an output device, such as 232.

Figure 3:
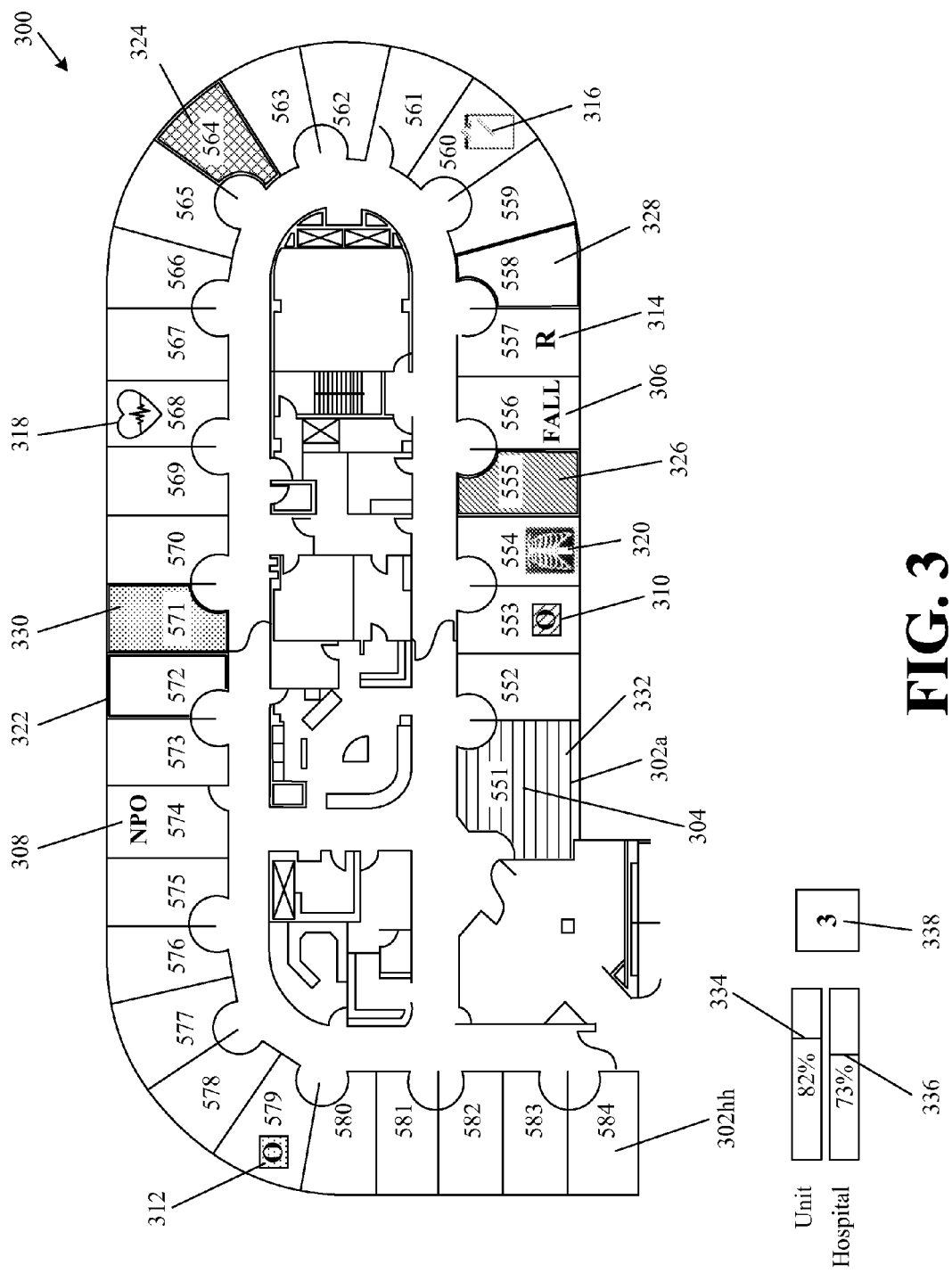
FIG. 3 illustrates an exemplary graphical user interface for the system of FIG. 1 in accordance with an embodiment of the invention.

In FIG. 3, an example of a graphical user interface 300 for an output device is shown. In the embodiment shown, an output device such as a display monitor can facilitate display of the graphical user interface 300 shown. The graphical user interface 300 can provide a geospatial arrangement of various information, such as graphical information, associated with a patient, including location information associated with a patient and an indicator of care of a patient. For example, the graphical user interface can include a map or geospatial view of a health care environment, such as a hospital. A map or geospatial view can be divided, for example, into multiple areas that represent the relative location of rooms in a hospital. One or more areas within or adjacent to the map or geospatial view can display graphical information associated with a status of a particular patient, such as location information associated with a patient or an indicator of care of a patient. Such areas within the map or adjacent to the map can include other graphical information including, but not limited to, text, icons, graphical elements, colors, timers, animation, or any combination thereof.

In one embodiment, one or more items associated with a particular room can be displayed within or adjacent to the representation of the room. For example, items such as beds, patients, health care personnel, instruments, tools, gurneys, wheelchairs, walkers, and other objects or persons in a health care environment can be displayed in a graphical user interface, such as 300. In this embodiment, an association between each item and a respective device capable of providing location information can be made by mounting a RFID tag or other location information type device to the item. Location information associated with a particular item can then be received by a query support engine, such as 126, and a representation of each item can be displayed via a graphical user interface for an output device. In this manner, various items can be displayed in a geospatial arrangement by a query support engine via a graphical user interface for an output device. This permits the graphical user interface to convey various amounts of graphical information about a particular activity for a particular patient. Items can be graphically represented by any combination of text, icons, graphical elements, colors, timers, animation, or any combination thereof.

In the embodiment shown in FIG. 3, location information associated with a patient can be displayed by the graphical user interface 300. Using either of the systems 100, 220 described above, or a system in accordance with an embodiment of the invention, a graphical user interface 300 can receive and display location information associated with a particular patient. As discussed above with respect to systems 100, 220, wireless location tracking technologies such as active RFID can allow one or more patients' locations to be tracked automatically as they move throughout a health care environment. For example, for a particular patient bed, such as 210 in FIG. 2, or room, such as 202, a graphical user interface 300 can display a patient location as, for instance, an icon or other graphical representation over the particular bed or room to permit a user to view a current patient location on the graphical user interface 300.

In the example graphical user interface 300 shown, consecutively numbered patient rooms 302*a*-302*hh*, in a counterclockwise orientation, on a particular floor of a hospital can be displayed within the map or geospatial view. Other rooms or areas in the map or geospatial view may not have a corresponding room number, and a respective room number may not be displayed for such rooms or areas, such as a corridor, hallway or monitoring area. A representation of rooms for a building, floor, or environment may be a relatively simple layout or general floor plan, and does not need to be to scale or depict an actual aspect ratio, door location, or orientation of the actual room, floor, building, or environment. Any layout, format, or representation of rooms in relation to each other can be used for a map or geospatial view of an environment, and may change based on some or all of the following: a user, user's role, location, time, date, or patient care event.

Text 304 for corresponding room numbers, such as "551" through "584", can be displayed relative to the respective patient rooms 302*a*-302*hh*. Other text can be displayed relative to a room, for instance, a patient safety indicator or a physician name. In one example, text with a patient safety indicator, such as the term "FALL" 306 or "NPO" 308, can indicate a heightened risk of falling or nothing by mouth, respectively, for a patient in a particular room. In another embodiment, any text can be used to represent various rooms, patient safety indicators, physician names, patient care states, activities, or other indicators of care of a patient.

Other graphical information such as an icon can be displayed within or adjacent to a room on a graphical user interface, such as 300. An icon can represent, for example, a patient care state or activity such as a new order, a patient location, or a step in a patient care process. By way of example, an "O"-shaped icon of a first color 310, such as blue, can be displayed within or adjacent to a particular room to indicate a patient with an unfulfilled order having normal priority. In another example, an "O"-shaped icon of a second color 312, such as red, can be displayed within or adjacent to a particular room to indicate a patient with an unfulfilled order having urgent ("stat") priority. Examples of a patient care state can include, but are not limited to, inpatient, outpatient, ready for discharge, ready for transfer, and whether patient's room is under isolation to avoid infection, scheduled or expected discharge time. Examples of a patient care activity can include, but are not limited to, whether a newly arrived patient has been seen by a nurse yet.

In another example, a "R"-shaped icon 314 can be displayed within or adjacent to a particular room to indicate that a new laboratory result associated with the patient is available, which may or may not be displayed by the graphical user interface. By way of another example, a "clipboard and thermometer" icon 316 can be displayed within or adjacent to a particular room to indicate a respective patient who has not yet had their vital signs recently taken or measured. In yet another example, a heart-shaped icon 318 can be displayed within or adjacent to a particular room to indicate that the patient is in a cardiology lab or department. In another example, a "x-ray" icon 320 can be displayed within or adjacent to a particular room to indicate a respective patient is in a radiology lab or department. In another embodiment, any combination of icons can be used to represent various patient care states, activities, or other indicators of care of a patient.

Graphical information such as graphical elements can be displayed within or adjacent to a room on a graphical user interface, such as 300. A graphical element can represent, for example, a special patient care state such as a patient on isolation. For example, a graphical element can be an outline 322 highlighting some or all of a particular room to indicate a special care state of a patient in the room. In another embodiment, any combination of graphical elements can be used to represent various patient care states or other indicators of care of a patient.

Graphical information such as colors can be displayed within or adjacent to a room on a graphical user interface, such as 300. A color can represent, for example, a particular patient care state, such as an inpatient or observation patient, or a representation of a room state, such as an unoccupied room or an unclean room. By way of example, a room shaded a first color 324 such as green can indicate a patient in a particular room is an inpatient. In another example, a room shaded with a second color 326 such as blue can indicate a patient in a particular room is under observation or an observation patient. In yet another example, a room without any color shading 328 can indicate an unoccupied room. In still another example, a room shaded with a third color 330 such as brown can indicate a room that is unclean. In another embodiment, any combination of colors can be used to represent various patient care states or other indicators of care of a patient.

Graphical information such as timers can be displayed within or adjacent to a room on a graphical user interface, such as 300. A timer can represent, for example, a starting time, an ending time, or both, for a particular patient care event. In another example, a timer can indicate how long a patient in a particular room has been in observation. In one embodiment, a timer can be displayed adjacent to or within a room or other area displayed on a graphical user interface, such as 300, to represent a duration of time that a patient has been in a particular room or area. In some instances, a timer can be incorporated in an icon or other type of graphical element or feature. In this manner, a user can monitor a patient's location as well as the duration of the patient's movement in particular rooms or areas, thus saving time for health care personnel and improving patient safety.

Graphical information such as animation can be displayed within or adjacent to a room on a graphical user interface, such as 300. Animation can include, for example, any movement, rotation, flashing, fading, cycling, or any combination of activity by graphical information thereof. For example, animation such as an alternating green-colored line pattern 332 can represent a patient for whom a doctor has written a discharge order.

Other types of graphical representations or techniques can be used to represent an item and convey graphical information about a particular activity for a particular patient in a graphical user interface, such as 300, for an output device, map, or other geospatial view in accordance with embodiments of the invention.

In the lower portion of the graphical user interface 300, one or more graphical indicators, such as capacity indicators 334, 336, 338, can be displayed. A capacity indicator can represent any characteristic of the health care environment to accommodate additional patients. For example, one capacity indicator can be a bar graph 334 indicating a unit capacity, such as 82%. Unit capacity can be a representation of the capacity of a particular group within a health care environment, such as a building floor or patient care group, and the ability of the particular group to accommodate additional patients. In another example, a capacity indicator can be another bar graph 336 indicating hospital capacity, such as 73%. Hospital capacity can be a representation of the capacity of a particular health care environment, such as a hospital or assisted care facility, and the ability of the particular health care environment to accommodate additional patients. By way of example, a capacity indicator can be a numeric FIG. 338, such as "3", indicating a critical shortage of some type of bed or the criticality of capacity utilization in a health care environment.

In the embodiment shown in FIG. 3, the map, geospatial view, and other display areas of the graphical user interface 300 can be dynamically updated in real time by a query support engine, such as 126 in FIG. 1, as new or updated information is determined, received, or otherwise detected, such as when a patient care event occurs. Examples of patient care events can include, but are not limited to, a new order associated with a patient, a new order associated with medicine or a medical procedure or measurement, results from a lab or department, a prescription approval, a new or updated patient location, a new or updated patient care status, a new physician or health care person assignment, and a new or updated contact for a patient.

In one example, a patient care event can be a new order placed by, or on the behalf of, a particular patient. If, for instance, a user desires to create a new order for a patient, a user, such as 112 in FIG. 1, can transmit new order information from a client device, such as 104a, to a query support engine, such as 126. The query support engine 126 can generate and facilitate a display of graphical information via a graphical user interface for an output device, such as displaying an "order" icon or "O", on the graphical user interface, such as 310. The order icon can be positioned on the graphical user interface 300, relative to a pre-existing graphical representation of a location where the particular patient is, such as a room or bed on a map or other geospatial-type view. When a user, such as 112, views the graphical user interface 300, the order icon can notify or otherwise inform the user or other health care personnel about the existence of the user's new order for the patient.

Often times multiple patient care events can occur simultaneously or in overlapping durations of time. In one embodiment, a graphical user interface for an output device can facilitate the display of multiple, simultaneous pieces of information. In one instance, multiple display areas can be defined within a single item, such as a room. Each display area within the particular item can display various types and amounts of information, such as orders, or patient safety information. In this manner, various types and amounts of information, such as text, an icon, and timers, can be displayed with respect to a particular item, such as a room.

In another embodiment, if a particular display area for a single item, such as a room, has multiple pieces of information to display, the multiple pieces of information can be sequenced in a predefined manner. For example, if the multiple pieces of information exist, each piece of information can be rotated through the display area relatively quickly, thus permitting a user to view some or all relevant patient information in the display area. The time each piece of information is displayed in a particular display area can be configurable or predefined by a user or via a query support engine, such as for two to three seconds.

In another example, multiple orders for a patient can be displayed by corresponding order icons positioned adjacent to a representation of a patient's location, such as a room. In another example, a status of results from one or more laboratories or departments, such as radiology, can be displayed by corresponding order icons positioned adjacent to a representation of a patient's location, such as a room. Other examples of patient care events can include, but are not limited to, approval of a pharmacy prescription, a new or existing patient location, a patient safety indicator such as a risk (fall, NPO) or medical condition (deaf), a patient status timer, a physician name, a nurse name, a care provider name, contact information, and a request for communication with others.

Some or all types of patient care events can be simultaneously displayed via a graphical user interface, such as 300, for an output device in a map, or other geospatial view.

In another embodiment, information associated with each item displayed on a graphical user interface can change over time, and new or changed information can automatically be added or updated via a graphical user interface in real time or as information is received. For example, a doctor can write a new order for a patient in a particular room. When the doctor or other health care personnel transmits via a client device, such as 104a, the order information to a query support engine, such as 126, the query support engine can facilitate display of a corresponding graphical representation of the order information via a graphical user interface for an output device. In this instance, the patient care event of writing a new order can result in an "order" icon being displayed over the room displayed by the graphical user interface, such as an "O" icon displayed over a graphical representation of the particular room on a map. Likewise, if the doctor cancels or modifies the new order for the patient in the particular room, the doctor or other health care personnel transmits the canceled or modified order information to the query support engine 126, and the query support engine can facilitate display of a corresponding graphical representation of the canceled or modified order information via the graphical user interface for an output device. In this instance, the patient care event of canceling or modifying an order can result in an "order" icon being removed from the display of the room shown via the graphical user interface, such as an "O" icon removed from a graphical representation of the particular room on a map.

Embodiments of the invention can process various types of user queries for information in a health care environment, and can also display various types of formatted or unformatted responses to queries in a graphical user interface for an output device. The examples and embodiments provided herein are by way of example and are not intended to be limiting.

In one embodiment, a user, such as 112, can utilize a client device, such as 104a, to generate and transmit a query for selected information to a query support engine 126, database 130, or other data storage device. In response to the user's query, the query support engine, database, or other data storage device can process the query to generate and return a query response. The query support engine can determine information in response to the query, and transmit the information and query response to the client device utilized by the user. The query support engine 126 can also facilitate a display of graphical information in a geospatial arrangement based at least in part on the query response on an output device associated with the client. For example, a user can transmit a query for a particular patient's information to a query support engine such as 126. In response to the user's query, the query support engine 126 can determine a response to the query, and if needed, can communicate with a database, such as 130, or other data storage device to obtain requested patient information in response to the query. The query support engine 126 can return selected information, i.e. patient information, to the user via the client device 104a in response to the user query. The query support engine 126 can also facilitate the display of a graphical representation of some or all of the patient information via a graphical user interface, such as 300, for an output device, such as 110.

In another example, a subset of items may be of particular interest to a user based on a user's particular role, location, or other context-type criteria. The user can generate and transmit a predefined query or set of instructions based in part on at least the user's particular role, location, or other context-type criteria, to a query support engine, such as 126. In response to the user's query, the query support engine 126 can determine a response to the query or set of instructions, and if needed, can communicate with a database, such as 130, or other data storage device to obtain information in response to the query. The query support engine 126 can return information based in part on at least the user's particular role, location, or other context-type criteria to the user via the client device 104a in response to the user query. The query support engine 126 can also facilitate the display of a graphical representation of some or all of the information via a graphical user interface, such as 300, for an output device, such as 110. In this manner, a context sensitive response to a user's predefined query or set of instructions can be provided.

In yet another example, a response to a user query can return a different set of items when the initial query is processed at different times. For example, if an initial user query is for "empty" rooms in a particular health care environment, then a set of rooms which meet this condition, "empty," can change as one or more patients move into and out of rooms over a particular period of time. As a patient moves into or out of a room, location information associated with the particular patient can be received by a query support engine, such as 126, and the query support engine can process the location information. If, for instance, the query support engine 126 facilitates a graphical display of a particular set of rooms on a graphical user interface, such as 300, as "empty," the query support engine can update and modify the set of rooms being displayed on the graphical user interface in real time as a change or modification to the query response occurs, i.e. the set of rooms that meets the "empty" condition.

In another embodiment, information provided in a query response can be modified, deleted, or updated based on an event, such as a completion event. If, for example, a piece of information is displayed in a graphical user interface, such as 300, an event may occur that determines when that piece of information is to be removed from the graphical user interface. Upon detection or determination that the particular event has occurred or is occurring, the particular piece of information can be removed from display on the graphical user interface. In this example, an event can be a completion-type event. A completion-type event can be, but is not limited to, an activity capable of being tracked by a health care information system such as admission, transfer, or discharge of a patient; an indication by a user via a client device that information should be removed; and expiration of a particular item over a predefined amount of time. A predefined amount of time can be, but is not limited to, a relative amount of time when a first display of information, such as 20 minutes; an absolute time such as midnight or 3:00 a.m.; or a calculation based at least in part on the information or context of the information, e.g. 15 minutes if not critical, or 60 minutes if critical.

In yet another embodiment, some or all information provided in a query response can be automatically modified, deleted, or updated based on time relative to an event. For instance, rather than a user indicate via a client device an occurrence or termination of a particular event to effect the removal of the information, a query support engine, such as 126, can automatically or otherwise determine when to remove, modify, or update the information based on a relative time since initiation or start of an event.

In one embodiment, the appearance of a graphical representation of information, such as text or an icon, can change over a period of predefined time or upon detection, determination, or completion of an event. In one example, graphical information such as an icon can visually change appearance as time elapses. If, in this example, a user does not act or otherwise respond to relatively critical event graphically represented by text or an icon, then the critical event can change color or change effects, e.g. start flashing or become animated, to indicate that attention of a user is needed. In yet another example, a graphical representation of information, such as text or an icon, can fade over a predefined period of time. In this instance, an icon representing a status of patient care or an event can be displayed in a graphical user interface, such as 300, with an initial opacity of approximately 100%. Over a predefined period of time, such as 24 hours, the icon can slowly fade to a relatively lower opacity such as approximately 25%. In this manner, graphical representation of the relative age of information such as a status of patient care or an event can be viewed in a graphical user interface.

In some embodiments, one or more users, such as 112, may desire to view information in more than one format. Embodiments of the present invention can display information in any number of desired formats, such as a geospatial view in the form of a map (shown in FIG. 3), or a view based on a selected subset of items such as rooms, patients or beds. Other selected subsets of information can be in the form of a user query over some or all of a population of items.

If a user query has been generated, or if information or a query response has been returned in response to a user query, a user can view the information or query response in a variety of different forms. For example, if a query response includes information, such as items, in a particular geographic area, then displaying the information and items in a graphical user interface including a map or geospatial view, such as 300 in FIG. 3, may be suitable since users may be accustomed to relating to such information or items in geographic-type terms. If the information and items in response to a query do not share a common geographic area, then other displays, views, or models can be used in accordance with embodiments of the invention. For instance, a suitable display, view, or model can include a grid or table view, where one or more items can be displayed in any number of rows and columns. In one example, up to six items or pieces of information could be displayed in a table or grid-type view comprising three columns and two rows. Any number of rows and columns can be displayed in a table or grid-type view in accordance with other embodiments of the invention.

Figure 4:
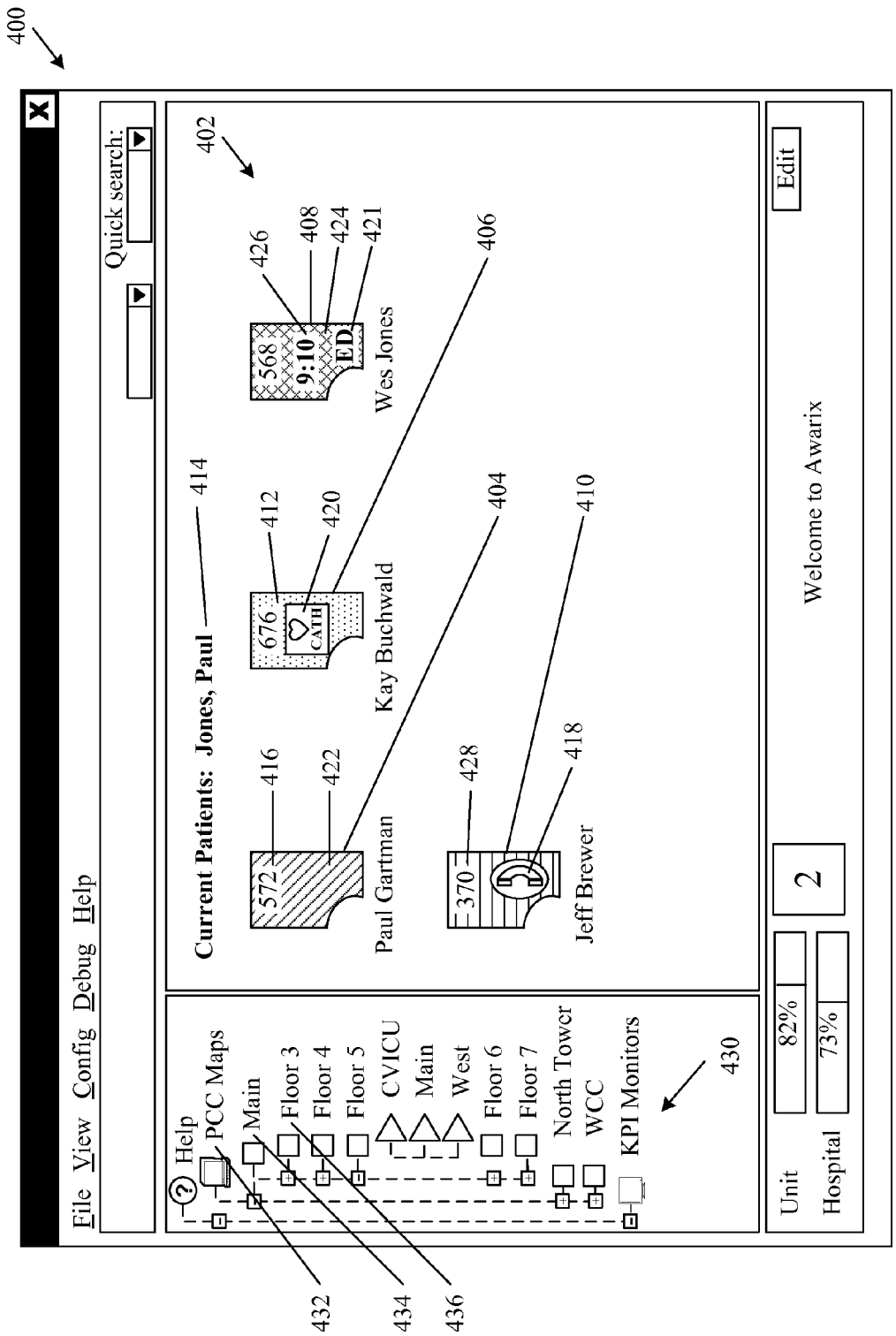
FIG. 4 is another graphical user interface in accordance with an embodiment of the invention.

FIG. 4 illustrates an example of another graphical user interface 400 for an output device in accordance with the invention. In the embodiment shown, an output device such as a display monitor can facilitate display of the graphical user interface 400. The graphical user interface 400 can include a table 402 or grid view of one or more items in a health care environment, such as a hospital. In the example shown, graphical representations of rooms 404, 406, 408, 410 can be displayed in response to a user query. One or more areas 412 within or adjacent to each of the graphical representations of each room 402 can display graphical information 414 associated with a status of a particular patient, such as a location of a patient or a status of a patient's care. The areas 412 within each of the graphical representations of each room 404, 406, 408, 410 can include various types of graphical information including, but not limited to, text, icons, graphical elements, colors, timers, animation, or any combination thereof.

As an example, a query from a user can inquire whether patients of "Dr. Paul Jones" are currently in a particular hospital. The user, such as 112 in FIG. 1, can transmit the query via a client device, such as 104a, to the query support engine, such as 126. The query support engine 126 can process the query to determine a query response, and can communicate with the database 130 or other data storage device to receive or obtain information if needed. In response to the query, the query support engine 126 can transmit a query response to the user 112 via the client device 104a. The query support engine 126 can facilitate a display of the query response on a graphical user interface, such as 400, for an output device, such as 110. In the example shown in FIG. 4, a response to the user query can include a table 402 indicating that Dr. Jones has four patients in four respective rooms. Various graphical information can be displayed in the table including but not limited to, text, icons, graphical elements, colors, and animation. In this instance, graphical representations of each of the four rooms 404, 406, 408, 410 are displayed below text 414 indicating the doctor's name, "Jones, Paul." Respective areas 412 within each of the graphical representations of each room 404, 406, 408, 410 can display other text 416 indicating the respective room number for each patient, such as the text "572", "575", "568", and "370". Within two of the graphical representations of rooms 406, 410, respectively, are icons indicating a status of patient care for the particular patient in the room, such as a "phone" icon 418 indicating that the case manager desires to speak with a doctor or other health care provider, and a "heart CATH" icon 420 indicating that the patient is currently in a cardiology lab or department. Furthermore, a graphical element such as an outline 418 can highlight some or all of a particular room, such as 406, to indicate a special care state of a patient in the room. Rooms, such as 406, 408, shaded with a first color 422 such as green can indicate a patient in the particular room is an inpatient. A room, such as 410, shaded with a second color 424 such as blue can indicate a patient in a particular room is under observation or an observation patient. In addition, a timer 426 is displayed in one room, such as 410, to indicate how long a patient in a particular room has been in observation. A room, such as 408, can include animation 428 such as an alternating green-colored line pattern, which can represent that the patient's doctor has written a discharge order for the patient. Other types of graphical information can be used to represent information in a graphical user interface for an output device in accordance with embodiments of the invention. In this manner, a user can graphically view information associated with some or all of his or her patients including location information and a status of patient care for each patient.

In one embodiment, a user can generate and store multiple views of information, such as information that is interesting to the user. As needed, the user can store and retrieve each view as needed. In one embodiment, one or more views can be organized in a selection tree on a graphical user interface, such as 400, to allow user access and navigation to the various views. For example, as shown in FIG. 4, a selection tree 430 is positioned adjacent to the left portion of the view 402, The selection tree 430 shown includes a hierarchical structure with a root folder 432, shown here as "PCC Maps", containing multiple building sub-folders 434, such as "MAIN", "North Tower", and "WCC" for a particular health care facility. Each of the building sub-folders 434 include one or more building floors 436 or other area maps or views, for instance "Floor 3", "Floor 4", "Floor 5", "Floor 6", and "Floor 7". Each floor, area map or view can be further subdivided into sub-areas, shown here as "CVICU", "Main", and "West". Using an input device (not shown), such as a keyboard or a mouse, associated with a client device, such as 104, a user can access and navigate between some or all of the folders 432, sub-folders 434, and floors 436, areas, or other views. Other embodiments can include fewer or greater numbers of root folders, sub-folders, and floors or other areas depending on the configuration and layout of the health care environment of interest. In another embodiment, a map or geospatial-type view can include other configurations, tree-type structures organized into multiple geographic areas, such as campus, building, floor, unit, etc.

Figure 5:
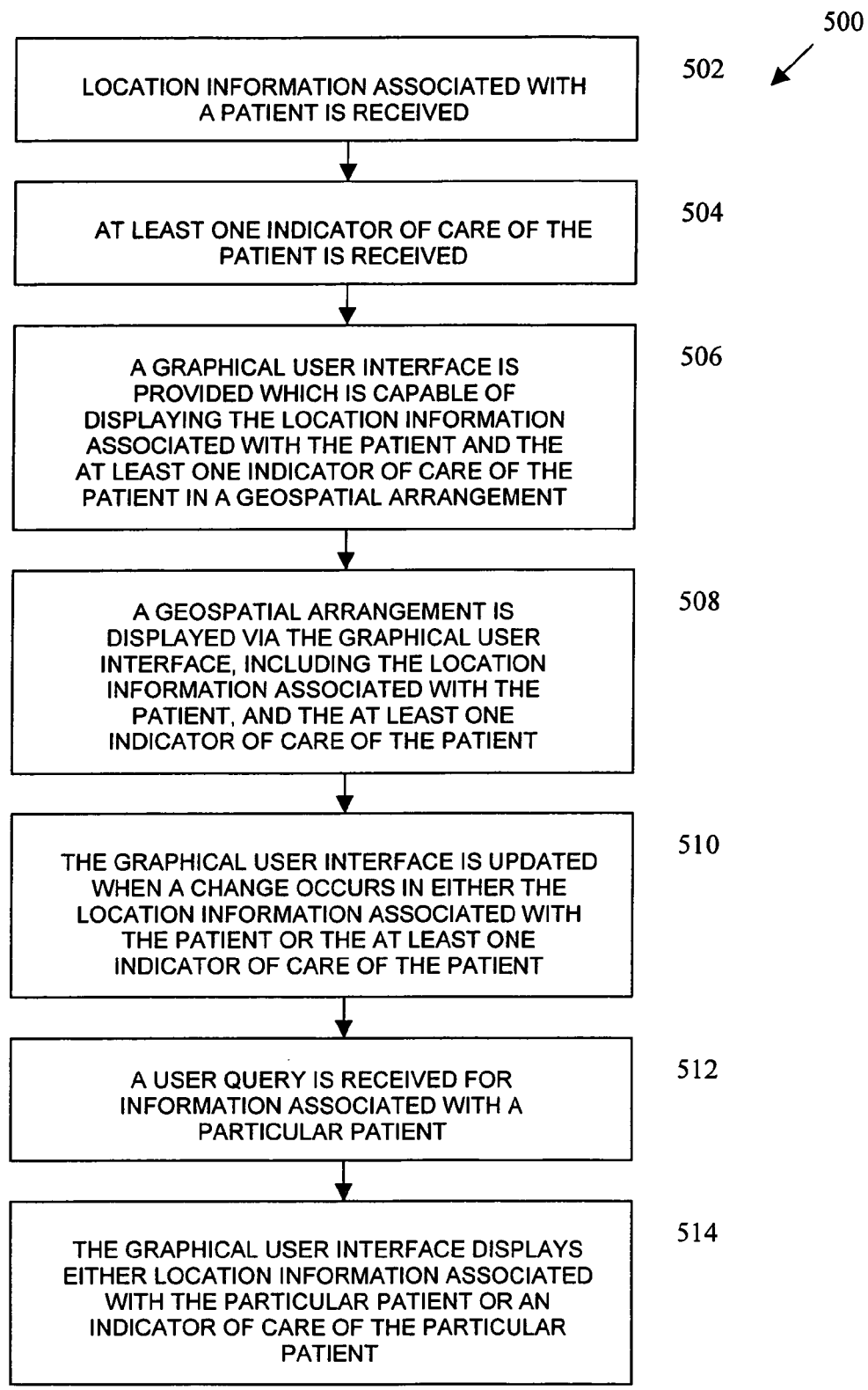
FIG. 5 is a flowchart diagram of an exemplary method in accordance with an embodiment of the invention.

FIG. 5 is a flowchart for an exemplary method in accordance with an embodiment of the invention. The method 500 shown can provide information associated with care of a patient in a health care environment. The method 500 can be implemented by the system 100 shown in FIG. 1. Other methods in accordance with embodiments of the invention can have fewer or additional steps than the method 500 described below.

The method 500 begins in block 502. In block 502, location information associated with a patient is received.

Block 502 is followed by block 504, in which at least one indicator of care of the patient is received.

Block 504 is followed by block 506, in which a graphical user interface is provided which is capable of displaying the location information associated with the patient and the at least one indicator of care of the patient in a geospatial arrangement.

Block 506 is followed by block 508, in which a geospatial arrangement is displayed via the graphical user interface, including the location information associated with the patient, and the at least one indicator of care of the patient.

Block 508 is followed by block 510, in which the graphical user interface is updated when a change occurs in either the location information associated with the patient or the at least one indicator of care of the patient.

Block 510 is followed by block 512, in which a user query is received for information associated with a particular patient.

Block 512 is followed by block 514, in which the graphical user interface displays either location information associated with the particular patient or an indicator of care of the particular patient.

Figure 6:
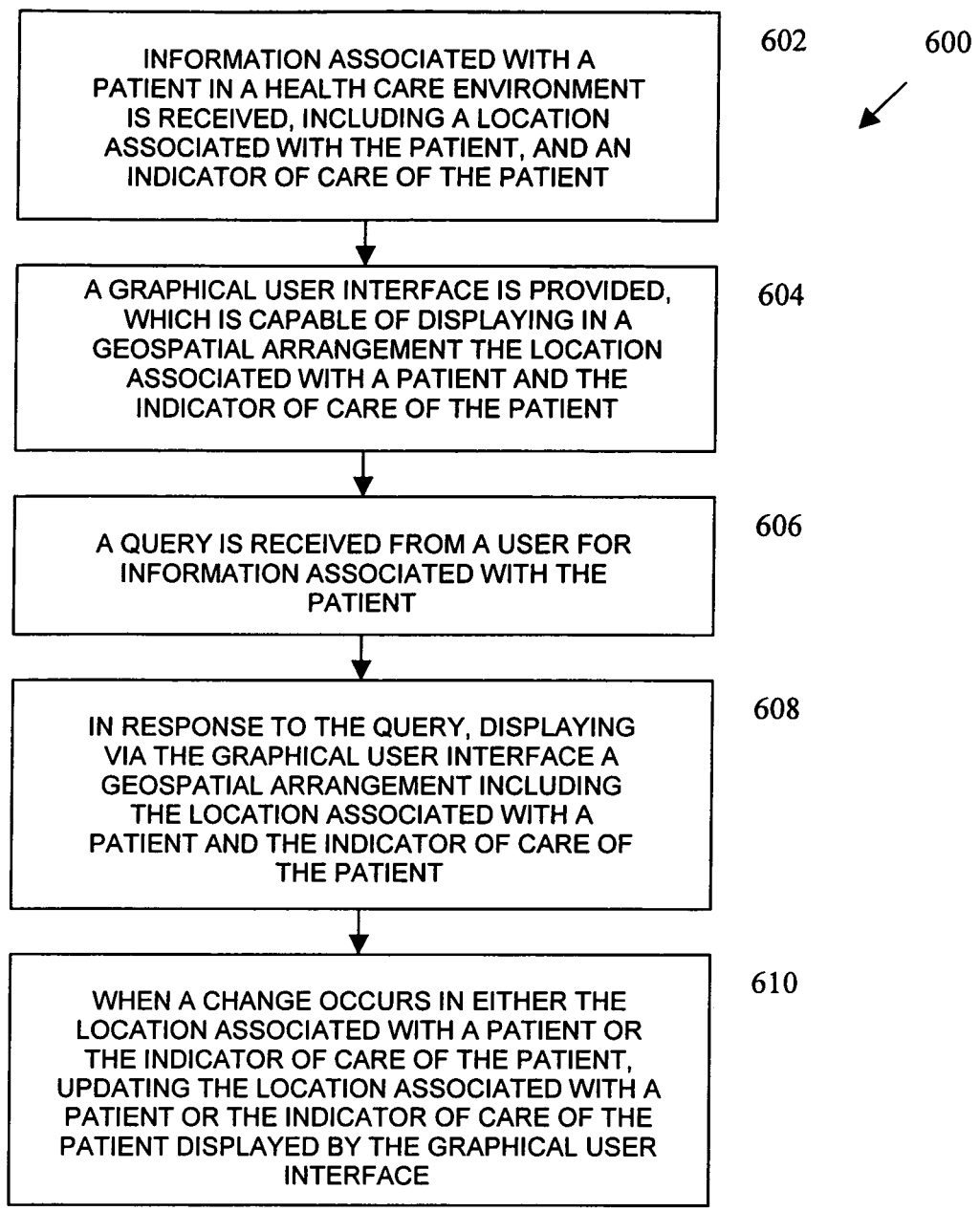
FIG. 6 is a flowchart diagram of another method in accordance with an embodiment of the invention.

FIG. 6 is a flowchart for another method in accordance with an embodiment of the invention. The method 600 shown can provide a result to a user query for information associated with care of a patient in a health care environment. The method 600 can be implemented by the system 100 shown in FIG. 1. Other methods in accordance with embodiments of the invention can have fewer or additional steps than the method 600 described below.

The method 600 begins in block 602. In block 602, information associated with a patient in a health care environment is received. The information can include a location associated with the patient, and an indicator of care of the patient.

Block 602 is followed by block 604, in which a graphical user interface is provided, which is capable of displaying the location associated with a patient and the indicator of care of the patient in a geospatial arrangement.

Block 604 is followed by block 606, in which a query is received from a user for information associated with the patient.

Block 606 is followed by block 608, in which, in response to the query, displaying via the graphical user interface a geospatial arrangement including the location associated with a patient and the indicator of care of the patient.

Block 608 is followed by block 610, in which when a change occurs in either the location associated with a patient or the indicator of care of the patient, updating the location associated with a patient or the indicator of care of the patient displayed by the graphical user interface.

While the above description contains many specifics, these specifics should not be construed as limitations on the scope of the invention, but merely as exemplifications of the disclosed embodiments. Those skilled in the art will envision many other possible variations that are within the scope of the invention as defined by the claims appended hereto.

The invention claimed is:

1. A method comprising executing computer implemented instructions performed by one or more processors for providing information associated with care of a patient in a health care environment, comprising:
   receiving, via at least one processor, location information associated with a plurality of patients;
   receiving, via at least one processor, patient care information from at least one of the following information systems: an ordering system, a result reporting system, a lab-type system, a pharmacy-type system, a radiology-type system, a transcription-type system, an environmental services-type system, or a transportation-type system;
   receiving, via at least one processor, information associated with at least one indicator of health care of at least one of the plurality of patients;
   providing a graphical user interface associated with a display mounted in the health care environment to display the location information associated with the plurality of patients, the patient care information, and the at least one indicator of health care of at least one of the plurality of patients in a geospatial map;
   displaying in a geospatial map via the graphical user interface the location information associated with the plurality of patients, the patient care information, and the at least one indicator of health care of the at least one of the plurality of patients;
   updating, via at least one processor, the graphical user interface when: (i) a change occurs in the location information associated with the plurality of patients, (ii) a change occurs in the patient care information, and (iii) when a change occurs in the at least one indicator of health care of the at least one of the plurality of patients;
   receiving a user query that comprises a request to display on the geospatial map via the graphical user interface the location information associated with a subset of the plurality of patients receiving care from a physician in the health care environment based on a particular user role, wherein the particular user role comprises at least one of: (i) a physician, (ii) a nurse or (iii) a healthcare assistant;
   receiving, based at least in part on the user query, a query response that comprises the requested location information for each of the one or more patients in the subset; and
   displaying, in response to the user query, the location information associated with each of the one or more patients in the subset on the geospatial map via the graphical user interface, wherein the location information comprises one or more indicators displayed adjacent to one or more patient rooms associated with each of the one or more patients in the subset.

2. The method of claim 1, further comprising:
   receiving another user query for information associated with the at least one of the plurality of patients; and
   displaying via the graphical user interface either location information associated with the at least one of the plurality of patients or an indicator of health care of the at least one of the plurality of patients.

3. The method of claim 1, wherein receiving location information associated with the plurality of patients comprises receiving a signal from a radio frequency identification device adjacent to the plurality of patients.

4. The method of claim 1, wherein receiving location information associated with the plurality of patients comprises detecting a radio frequency identification device adjacent to the plurality of patients.

5. The method of claim 1, wherein receiving location information associated with the plurality of patients comprises receiving a signal from a radio frequency identification device adjacent to a patient chart associated with each of the plurality of patients.

6. The method of claim 1, wherein receiving at least one indicator of health care of at least one of the plurality of patients comprises receiving at least one of the following: an order, a request, an approval, an approval of a prescription, a lab result, a safety indicator, a limit, a range, a warning, a statistic, a health status, a date, a time, a timer, contact information, a health-related statistic, a body function, patient care information, a patient care state, a special patient care state, or a patient care activity.

7. The method of claim 1, wherein the geospatial map comprises at least one of the following: a map representing at least a portion of the health care environment, or a geospatial-type view of at least a portion of the health care environment.

8. The method of claim 1, wherein displaying in a geospatial map via the graphical user interface the location information associated with the plurality of patients, the patient care information, and the at least one indicator of health care of the at least one of the plurality of patients comprises displaying at least one of the following: text, an icon, a graphical element, a color, a timer, or animation.

9. The method of claim 1, wherein the health care environment comprises at least one of the following: a room, a building, a hospital, an assisted care facility, or a medical care facility.

10. A method comprising executing computer implemented instructions performed by one or more processors for providing a result to a user query for information associated with a patient in a health care environment, comprising:
receiving, via at least one processor, information associated with a plurality of patients in a health care environment, comprising:
a location associated with the plurality of patients;
patient care information from at least one of the following information systems: an ordering system, a result reporting system, a lab-type system, a pharmacy-type system, a radiology-type system, a transcription-type system, an environmental services-type system, or a transportation-type system; and
an indicator of health care of at least one of the plurality of patients;
providing a graphical user interface associated with a display mounted in the health care environment to display in a geospatial map the location associated with the plurality of patients, the patient care information, and the at least one indicator of health care of the at least one of the plurality of patients in the geospatial map;
displaying via the graphical user interface in the geospatial map the location associated with the plurality of patients, the patient care information, and the indicator of health care of the at least one of the plurality of patients;
updating, via at least one processor, the graphical user interface when: (i) a change occurs in the location associated with the plurality of patients, (ii) a change occurs in the patient care information, and (iii) when a change occurs in the at least one indicator of health care of the at least one of the plurality of patients;
receiving a user query that comprises a request to display on the geospatial map via the graphical user the location associated with a subset of the plurality of patients receiving care from a physician in the health care environment based on a particular user role, wherein the particular user role comprises at least one of: (i) a physician, (ii) a nurse or (iii) a healthcare assistant;
receiving, based at least in part on the user query, a query response that comprises the requested location for each of the one or more patients in the subset; and
displaying, in response to the user query, the location associated with each of the one or more patients in the subset on the geospatial map via the graphical user interface, wherein the location information comprises one or more indicators displayed adjacent to one or more patient rooms associated with each of the one or more patients in the subset.

11. The method of claim 10, wherein a location associated with the plurality of patients comprises at least one of the following: a signal received from a radio frequency identification device adjacent to the plurality of patients; detection of a radio frequency identification device adjacent to the plurality of patients; or a signal received from a radio frequency identification device adjacent to a patient chart associated with each of the plurality of patients.

12. The method of claim 10, wherein an indicator of at least one of the plurality of patients comprises at least one of the following: an order, a request, an approval, an approval of a prescription, a lab result, a safety indicator, a limit, a range, a warning, a statistic, a health status, a date, a time, a timer, contact information, a health-related statistic, a body function, patient care information, a patient care state, a special patient care state, or a patient care activity.

13. The method of claim 10, wherein the geospatial map comprises at least one of the following: a map representing at least a portion of the health care environment, or a geospatial-type view of at least a portion of the health care environment.

14. A system for tracking a patient and monitoring care of the patient in a health care environment, comprising:
an output device to display a location associated with a plurality of patients and an indicator of health care of at least one of the plurality of patients in a geospatial map, wherein the output device comprises a display mounted in the health care environment; and
a query support engine capable of
receiving information associated with the plurality of patients in a health care environment, comprising:
the location associated with the plurality of patients;
patient care information from at least one of the following information systems: an ordering system, a result reporting system, a lab-type system, a pharmacy-type system, a radiology-type system, a transcription-type system, an environmental services-type system, or a transportation-type system; and
an indicator of health care of the at least one of the plurality of patients;
displaying in a geospatial map via the output device the location associated with the plurality of patients, the patient care information, and the indicator of health care of the at least one of the plurality of patients;
updating, via at least one processor, the output device when: (i) a change occurs in the location associated with the plurality of patients, (ii) a change occurs in the patient care information, and (iii) when a change occurs in the at least one indicator of health care of the at least one of the plurality of patients;

receiving a user query that comprises a request to display on the output device the location associated with a subset of the plurality of patients receiving care from a physician in the health care environment based on a particular user role, wherein the particular user role comprises at least one of: (i) a physician, (ii) a nurse or (iii) a healthcare assistant;

receiving, based at least in part on the user query, a query response that comprises the requested location for each of the one or more patients in the subset; and displaying, in response to the user query, the location associated with each of the one or more patients in the subset on the geospatial map via the output device, wherein the location comprises one or more indicators displayed adjacent to one or more patient rooms associated with each of the one or more patients in the subset.

15. The system of claim 14, wherein the output device comprises a graphical user interface capable of displaying a map of the health care environment.

16. The system of claim 14, wherein receiving information associated with the patient in a health care environment comprises at least one of the following: receiving a signal received from a radio frequency identification device adjacent to the plurality of patients; detection of a radio frequency identification device adjacent to the plurality of patients; or a signal received from a radio frequency identification device adjacent to a patient chart associated with each of the plurality of patients; or receiving input from a user via a client device.

17. A system for tracking a patient and monitoring care of the patient in real time in a health care environment, comprising:

an output device comprising a user interface, wherein the user interface displays in a geospatial map:

a plurality of indicators associated with respective locations associated with a plurality of patients in the health care environment;

a plurality of indicators associated with patient care information comprising at least one of the following: an approval of a prescription or a lab result;

a plurality of indicators associated with health care of the plurality of patients in the health care environment; and in response to a user query, a location associated with a subset of the plurality of patients receiving care from a physician in the health care environment based on a particular user role, wherein the particular user role comprises at least one of: (i) a physician, (ii) a nurse or (iii) a healthcare assistant, and wherein the location comprises one or more indicators displayed on the geospatial map adjacent to one or more patient rooms associated with each of the one or more patients in the subset, and wherein the user query that comprises a request to display on the geospatial map via the user interface the location associated with the subset of the plurality of patients receiving care from the physician.

18. The system of claim 17, wherein the geospatial map of a health care environment comprises a graphical representation of a plurality of rooms in the health care environment.

19. The system of claim 17, wherein the geospatial map of the health care environment can be updated when a change occurs to any of the plurality of indicators associated with respective locations associated with the plurality of patients in the health care environment, the plurality of indicators associated with health care of the plurality of patients in the health care environment, or the plurality of indicators associated with respective locations of each of the plurality of patients receiving care from the particular physician.

20. The system of claim 17, wherein the plurality of indicators associated with respective locations associated with the plurality of patients in the health care environment, the plurality of indicators associated with health care of the plurality of patients in the health care environment, and the plurality of indicators associated with respective locations of the plurality of patients receiving care from the particular physician can be displayed in response to a user query for information associated with at least one of the plurality of patients.

* * * * *